United States Patent [19]

Habermann et al.

[11] Patent Number: 5,298,603
[45] Date of Patent: Mar. 29, 1994

[54] GM-CSF PROTEIN, ITS DERIVATIVES, THE PREPARATION OF PROTEINS OF THIS TYPE, AND THEIR USE

[75] Inventors: Paul Habermann, Frankfurt am Main; Hubert Müllner, Kelkheim, both of Fed. Rep. of Germany

[73] Assignee: Hoechst Aktiengesellschaft, Frankfurt am Main, Fed. Rep. of Germany

[21] Appl. No.: 993,859

[22] Filed: Dec. 21, 1992

Related U.S. Application Data

[63] Continuation of Ser. No. 627,552, Dec. 14, 1990, abandoned, which is a continuation of Ser. No. 341,248, Apr. 20, 1989, abandoned, which is a continuation of Ser. No. 943,432, Dec. 19, 1986, abandoned.

[30] Foreign Application Priority Data

Dec. 21, 1985 [DE] Fed. Rep. of Germany ....... 3545568

[51] Int. Cl.$^5$ .............................................. C07K 13/00
[52] U.S. Cl. .................................... 530/351; 530/395; 530/825; 435/69.5; 435/69.52; 435/69.6; 930/140; 930/145; 930/144
[58] Field of Search ........................ 530/351, 395, 825; 435/69.5, 69.52, 69.6; 930/140, 145, 141

[56] References Cited

U.S. PATENT DOCUMENTS

| 4,438,032 | 3/1984 | Golde et al. ................... 260/112 R |
| 4,568,640 | 2/1986 | Rubin ................................ 435/70 |

FOREIGN PATENT DOCUMENTS

| 0128733A1 | 12/1984 | European Pat. Off. . |
| 0183350 | 9/1985 | European Pat. Off. . |
| 225701 | 6/1987 | European Pat. Off. . |
| 269455 | 6/1988 | European Pat. Off. . |
| 274560 | 7/1988 | European Pat. Off. . |
| 3267292 | 11/1988 | Japan . |
| 3276490 | 11/1988 | Japan . |
| 8504188 | 9/1985 | PCT Int'l Appl. . |
| WO8600639 | 1/1986 | PCT Int'l Appl. . |
| WO8603225 | 6/1986 | PCT Int'l Appl. . |

OTHER PUBLICATIONS

Clark Lewis et al., *J. Immunol.* 1986, vol. 141, pp. 881-889.
LaBranche et al., *Arch Biochem Biophys* vol. 276 (1) 1990, pp. 153-159.
Sasada et al., *Cell Struct. Funct.* 13(2) 1988, pp. 129-141.
Wong et al., *PNAS* 83, 1986, pp. 3233-3237.
Komings et al., *J. Shear Biol.* 127(1) 1987 pp. 63-78.
Wells et al. *Gene* 34, 1985, pp. 315-323.
Zaller et al., *Nuclear Acids,* vol. 10 (20) 1982, pp. 6487-6508.
H. Dalboge et al., "A Novel Enzymatic Method For Production Of Authentic hGH From An Escherichia Coli Produced hGH-Precursor", Bio/Technology, vol. 5: 161-164 (Feb. 1987).
Berzofsky, "Intrinsic and Extrinsic Factors in Protein Antigenic Structure," Science, vol. 229, pp. 932-940 (Sep. 6, 1985).
Benjamin et al., "The Antigenic Structure Of Proteins: A Reappraisal," Ann. Rev. Immunol., vol. 2, pp. 67-101 (1984).
Subramanian, *Biotechnology* vol. 3 1985, p. 597.
Sreft et al. *Science* 230, 1985, pp. 1171-1173.
Lee et al. *PNAS* 82, 1985, pp. 4360-4364.
Cantrell et al. *PNAS* 82, 1985, pp. 6250-6254.
Miyatake et al. *EMBO* 4(10) 1985, pp. 2561-2568.
De Lamater et al. *EMBO* 4(10) 1985 pp. 2575-2581.
Gough et al., *Nature* 309, 1984, pp. 763-767.
Stanley *EMBO* 4(10) 1985, pp. 2569-2573.
Kajigawa et al., *J. Exp. Med.,* 164, 1986, pp. 1102-1113.

*Primary Examiner*—Garnette D. Draper
*Attorney, Agent, or Firm*—Finnegan, Henderson, Farabow, Garrett & Dunner

[57] ABSTRACT

Expression of a gene coding for human granulocyte macrophage colony-stimulating factor (CSF) in bacteria results in CSF proteins which are biologically active. Modification of the natural or of a synthetic gene structure results in biologically active derivatives with a modified amino acid sequence.

1 Claim, 16 Drawing Sheets

FIG.1a
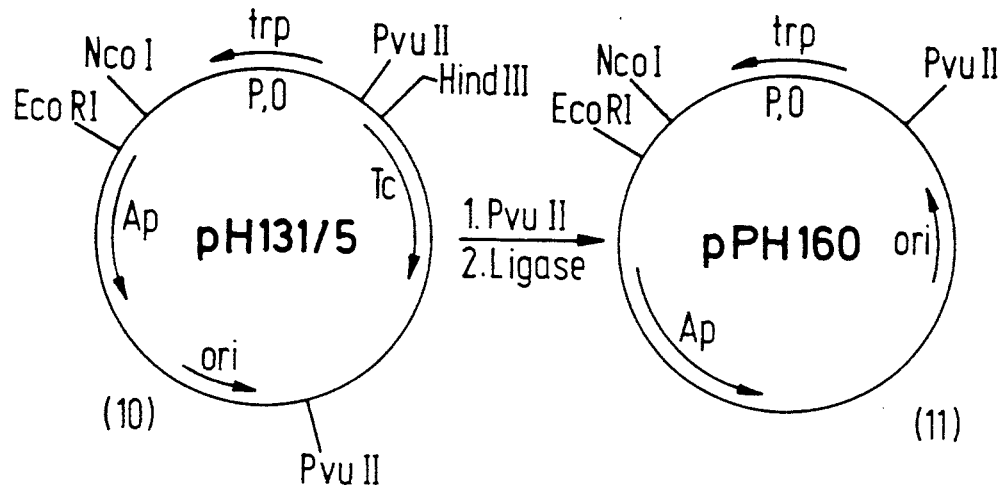
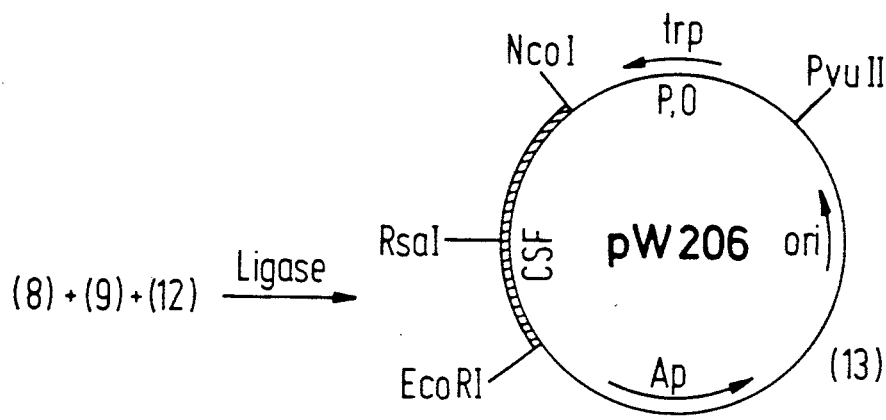

pKK 65-10 $\xrightarrow{EcoRI}$ EcoRI≠T1≠T2≠EcoRI    (14)

pUC12 $\xrightarrow[2.PstI]{1.EcoRI}$

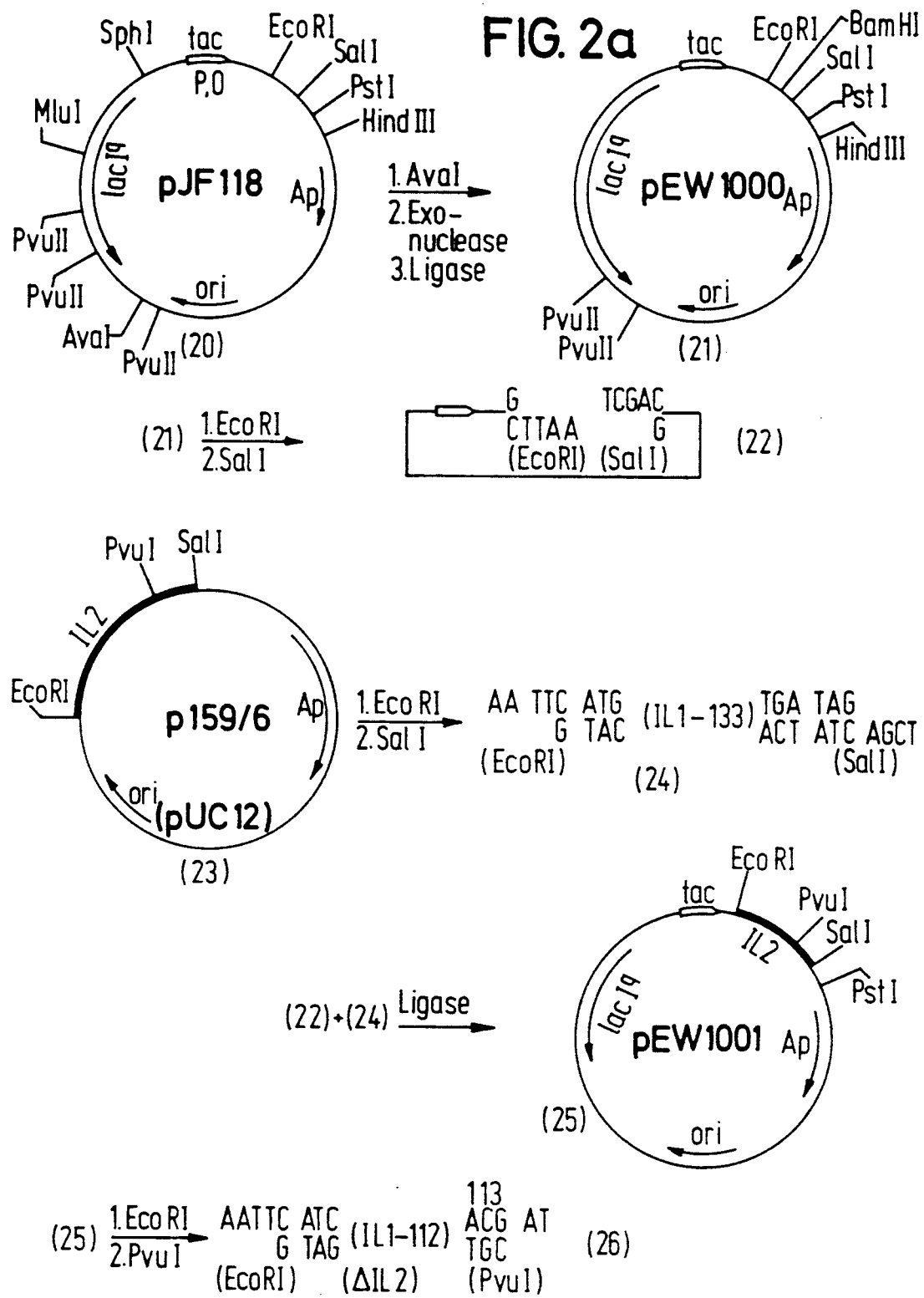

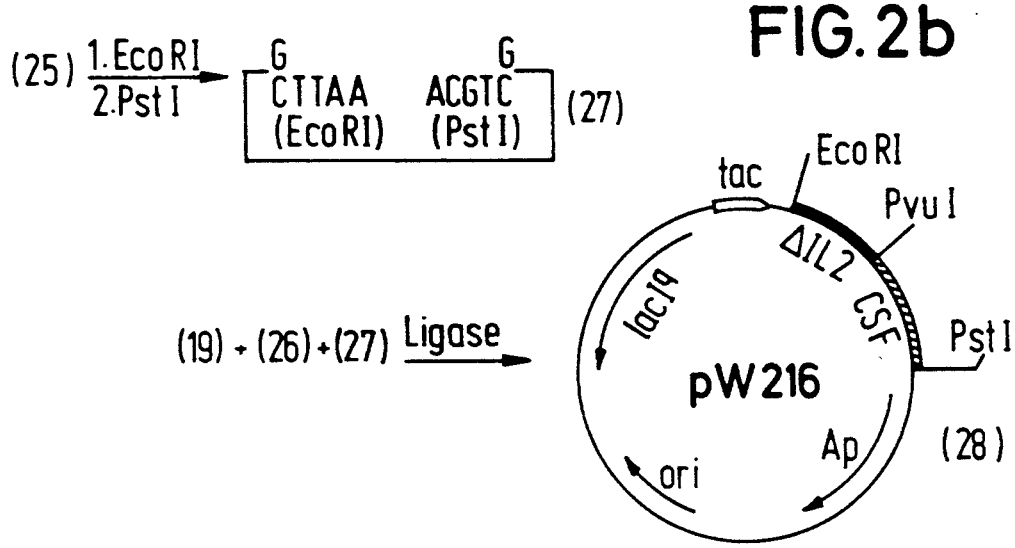
FIG. 2b
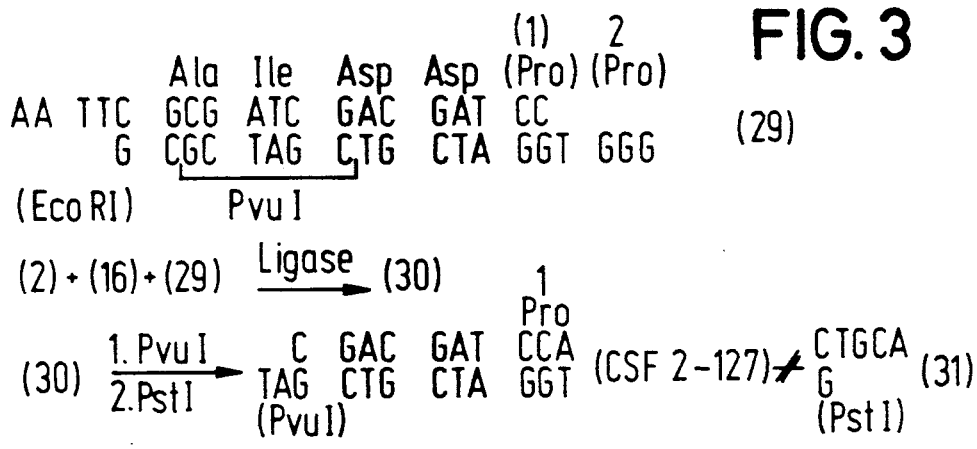
FIG. 3
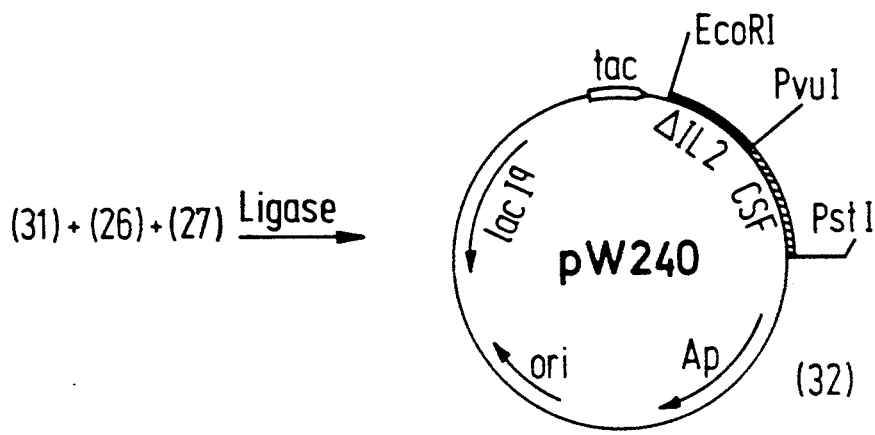

FIG. 4
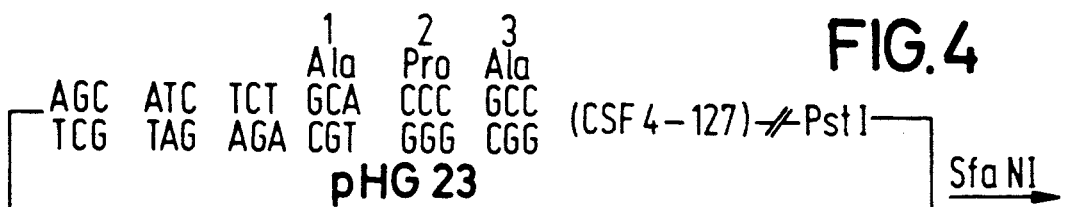
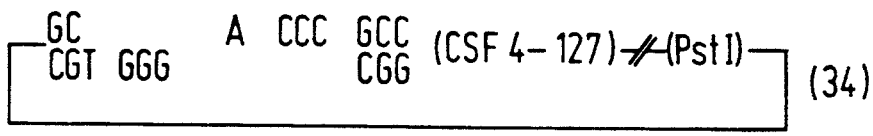
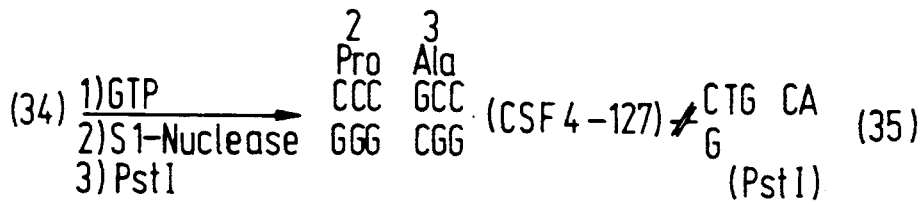
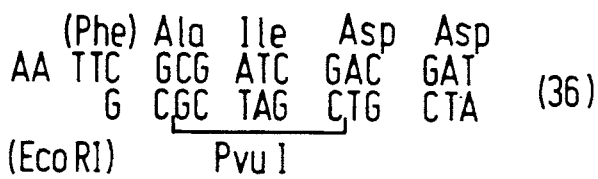
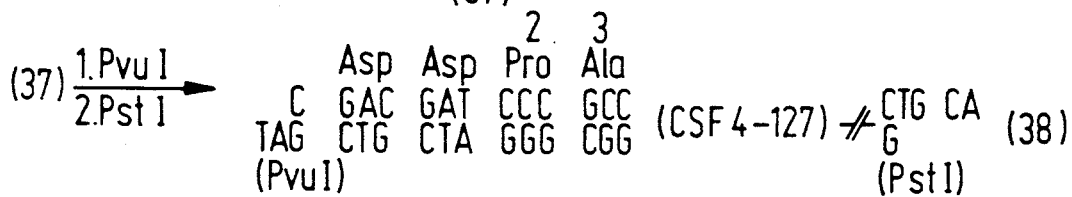
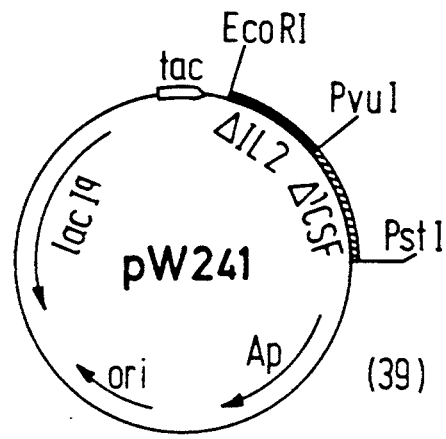

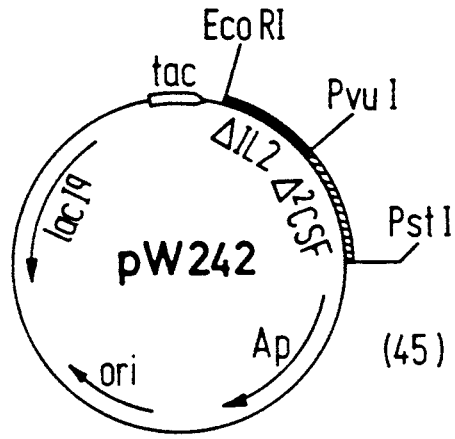

```
                    12
         Asp Asp  Pro
AA TTC GCG ATC GAC GAT CCC       (51)          FIG. 7
   G CGC TAG CTG CTA GGG A
(EcoRI)  (PvuI)         (BstNI)

(51) + (33) + (16)  Ligase→    (52)

(52)  1.PvuI→     (53)
      2.PstI

(53) + (26) + (27)  Ligase→  pW 244   (54)
```

```
                                      125    FIG. 8
          Asp Asp Pro                 Val
     BstNI    C GAC GAT CCG           GTC C
(19) ─────→   TAG CTG CTA GGC (CSF1-124) CAG GT   (55)
      part.  (PvuI)                        (BstNI)

(Ser)Ile Ser                125
     1.PstI      GC ATC TCT              GTC C
(33) ─────→  ACG TCG TAG AGA (CSF1-124)  CAG GT   (56)
     2.BstNI,    (PstI)                  (BstNI)
      part.
         Asp Stp Stp           PstI
     AG GAT TGA TAA GCT TTC TGC AGC CC    (57)
     C  CTA ACT ATT CGA AAG ACG TCG GG
   (BstNI)                        (SmaI)

pUC 13  1.PstI →   ┌CTGCA      GGG ┐
        2.SmaI    │ G          CCC │   (58)
                   │(PstI)    (SmaI)│
                   └                 ┘

(58) + (56) + (57)  Ligase→

125 126
                              Val Gln Asp Stp Stp   PstI      SmaI
   PstI Ser Ile Ser
  ┌C TGC AGC ATC TCT(CSF1-124)GTC CAG GAT TGA TAA GCT TTC TGC AGC CCGGG┐
  │G ACG TCG TAG AGA         CAG GTC CTA ACT ATT CGA AAG ACG TCG GGCCC│
  │                    pW 245                     HindIII             │
  └                                                                    ┘
                                                                    (59)
```

FIG.10
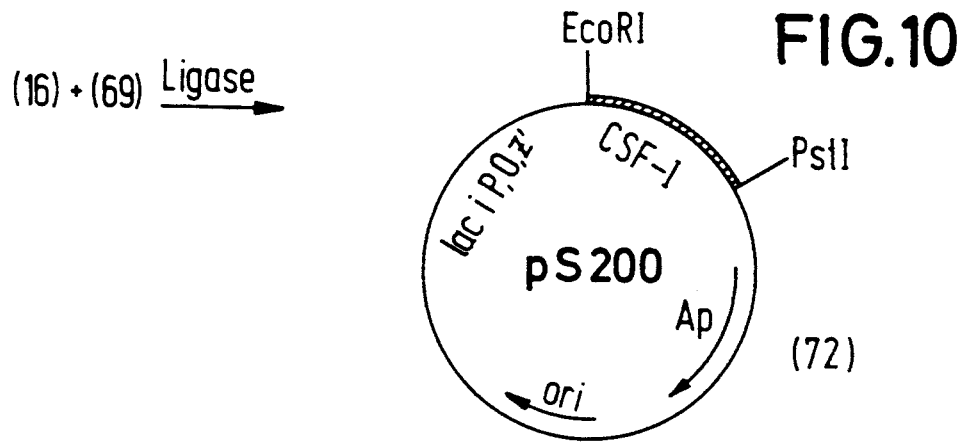
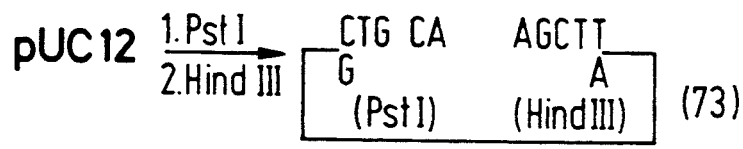
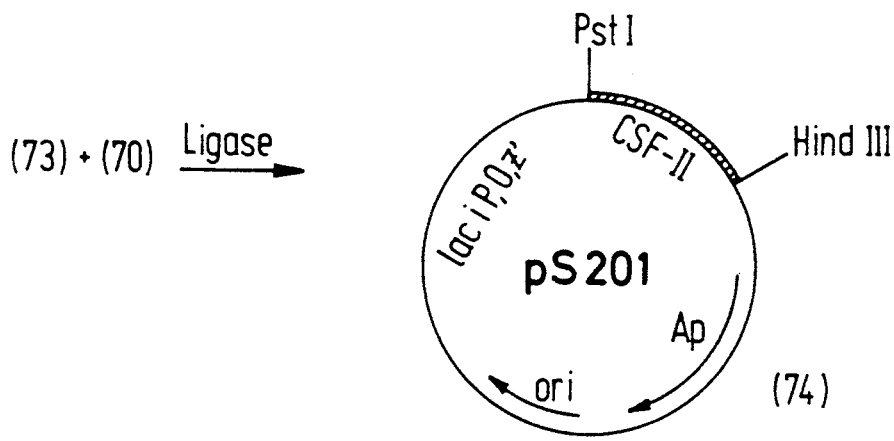
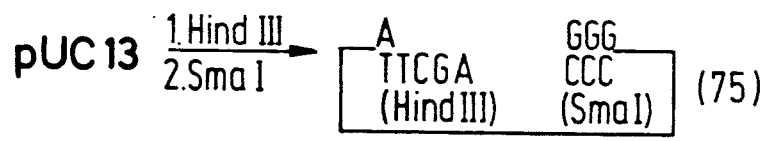
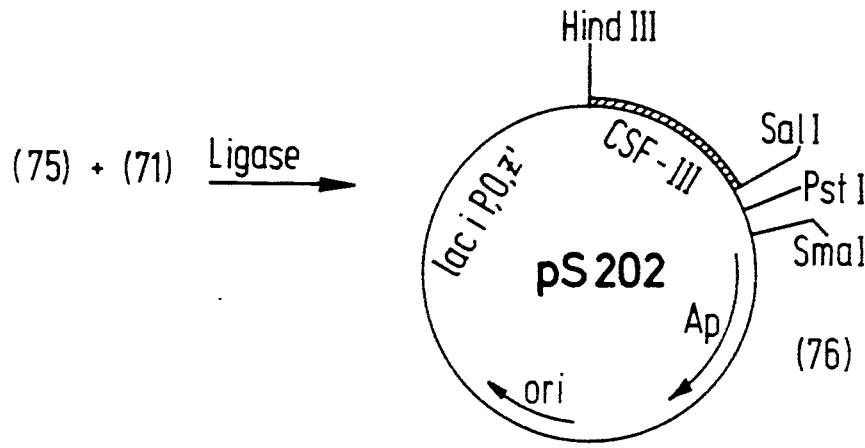

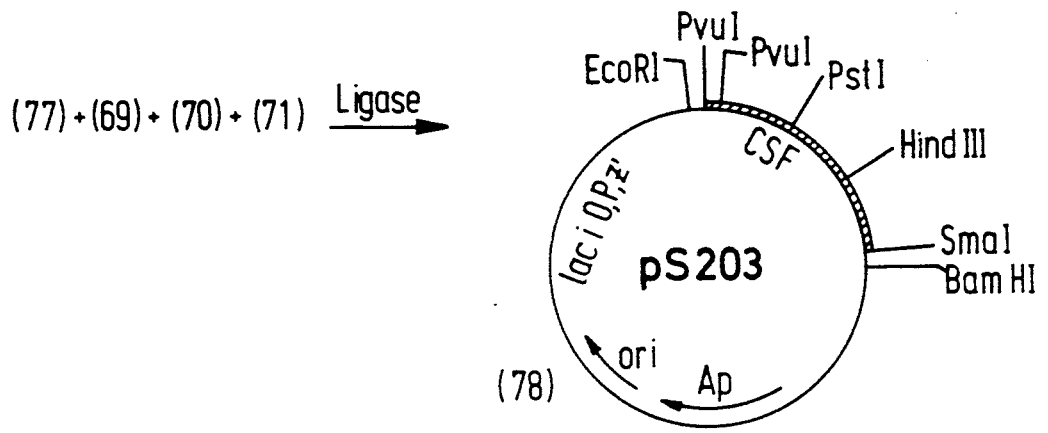
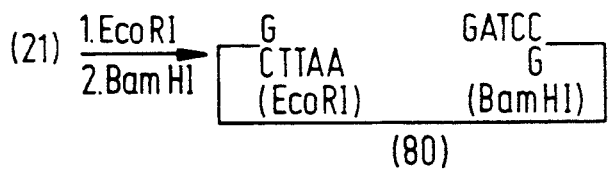
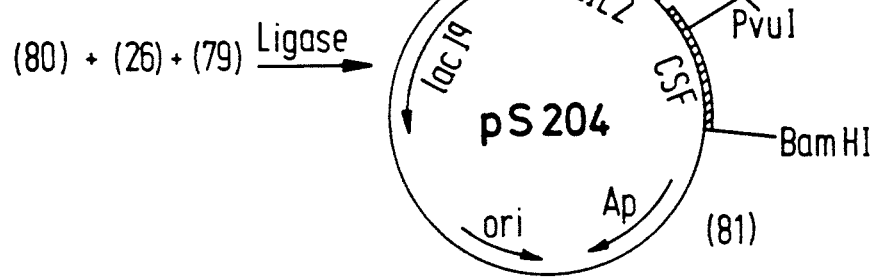
FIG. 10a

FIG.11

```
        PvuI              1    2    3    4    5    6    7    8
    (Ser) Ile Ala Trp   Ala  Pro  Ala  Arg  Ser  Pro (Ser)(Pro)
    AAT TCG ATC GCA   TGG  GCG  CCG  GCC  CGA  TCG  CCG              (82)
        GC  TAG CGT   ACC  CGC  GGC  CGG  GCT  AGC  GGC  AGA  GGC
   (EcoRI)

7    8    9   10   11   12  (13)  14   15   16
      (Ser)(Pro) Ser Thr  Gln  Pro  His  Glu  His  Val
       TCT  CCG TCG  ACC  CAG  CCC  CAC  GAA  CAC  GTT                (83)
            AGC TGG  GTC  GGG  GTG  CTT  GTG  CAA
                                                        (HpaI)

17
                                   Asn
         1) EcoRI        G          AAC
    (72) ─────────  ┌─          ─────────            ─┐
         2) HpaI    │ CTTAA     TTG    (CSF 18-50)    │              (84)
                    │ (EcoRI)  (HpaI)                 │
                    └─                               ─┘

┌─ EcoRI
                                                    │  ┌─ PvuI
                                                    │  │ ┌─ HpaI
    (84)+(82)+(83)  ─Ligase─►     ╱lac iPO_z╲  CSF-1
                                 ╱             ╲       ─ PstI
                                │    pS205      │
                                 ╲             ╱  Ap
                                  ╲           ╱
                                     ori
                                         (85)

73
                     (Leu)
         1. HindIII  AG CTT                        Stp  Stp
    (76) ──────────             (CSF 74-127)       TGA  TAG
         2. SalI        A                          ACT  ATC  AGCT     (86)  +
                    (HindIII)                                 (SalI)

PstI       SmaI
                              A       TCG  ACT  GCA  GCC  CGG  G
              +          ┌─ TTCGA          TA   CGT  CGG  GCC  C ─┐  (87)
                         │  (HindIII)                     (SalI)  │
                         └─                                      ─┘

(Leu)                    (Phe)
         TaqI      AGCTT                       TT
    (86)──────►          (CSF 74-118)         AAG  C                  (88)
                     A
                  (HindIII)                        (TaqI)

120  121 (122) 123  124  125  126  127
         Asp  Cys  His  Glu  Pro  Val  Gln  Glu  Stp  Stp
       C GAC  TGT  CAC  GAG  CCG  GTC  CAG  GAA  TGA  TAG             (89)
          TG  ACA  GTG  CTC  GGC  CAG  GTC  CTT  ACT  ATC  AGC T
       (TaqI)                                                  (SalI)
```

FIG.13

```
  33   34    35  (36)  37   38   39   40   41   42   43
(Ala) Ala  Glu   Ile  Asn  Glu  Thr  Val  Glu (Val)(Ile)
G GCC GCG GAA  ATC  AAC  GAA  ACC GTT  GAA                    (95)
  CGG CTT  TAG  TTG  CTT       TGG CAA CTT CAC TAT
(XmaIII)

42   43    44   45 (46)  47   48   49
(Val)(Ile)  Ser  Glu Leu  Phe  Asp (Leu)
GTG  ATA  TCT  GAG CTC  TTC  GAC CTG CA                      (96)
      AGA  CTC  GAG AAG  CTG G
                                    (PstI)
```

```
        1.PvuI
(72)  ─────────▶
        2.XmaIII                           32    33
                                          (Thr)(Ala)
                        CG               AC
                      T AGC  (CSF6-31)   TGC CGG               (97)
                       (PvuI)                  (XmaIII)

1    2    3    4
          Ile  Ala  Met  Ala  Pro  Ala (Arg)
AAT TCG  ATC  GCG  ATG  GCG  CCG  GCC CGA TC                  (98)
    GC  TAG  CGC  TAC  CGC  GGC  CGG G
(EcoRI)                                        (PvuI)
```

(16) + (98) + (97) + (95) + (96) ──▶ pS208   (99)

```
  73   74   75   76   77   78  (79) (80)  81
(Leu) Lys  Gly  Pro  Leu  Thr  Leu Leu (Ala)
AG CTT  AAG  GGG  CCC  CTC  ACC CTG CTG G                    (100)
    A  TTC  CCC  GGG  GAG  TGG GAC GAC CGA TC
(HindIII)                                        (NheI)
```

```
       1.HindIII        A              CTAGC
(76) ─────────────▶ ┌─ TTCGA              G ─┐              (101)
       2.NheI       │   (HindIII)     (NheI) │
                    └───────────────────────┘
```

(100) + (101) ──Ligase──▶ pS209   (102)

GM-CSF PROTEIN, ITS DERIVATIVES, THE PREPARATION OF PROTEINS OF THIS TYPE, AND THEIR USE

This application is a continuation of application Ser. No. 07/627,552 filed Dec. 14, 1990, now abandoned, which is a continuation of Ser. No. 07/341,248 filed Apr. 20, 1989, now abandoned, which is a continuation of Ser. No. 06/943,432 filed Dec. 19, 1986, now abandoned.

BACKGROUND OF THE INVENTION

Human granulocyte macrophage colony-stimulating factor (GM-CSF) is a glycoprotein with a molecular weight of about 23,000 dalton. The cDNA sequence and the expression of the glycoprotein in mammalian cells have already been disclosed (G. G. Wong et al., Science 228 (1985), 810–815, D. Metcalf, Science 229 (1985), 16–22).

SUMMARY OF THE INVENTION

It has now been found, surprisingly, that the expression of human GM-CSF protein, called "CSF" hereinafter, in bacteria results in a biologically active product. Thus the invention relates to CSF for use in medical treatment and to the use for the preparation of medicaments.

The invention furthermore relates to the preparation of CSF by expression in bacteria, in particular in *E. coli.* In particular, it is possible to use for this purpose the published cDNA sequences which can be obtained in a manner known per se, preferably by synthesis.

The invention additionally relates to expression vectors for use in bacteria, in particular in *E. coli,* which contain, in a suitable arrangement ("operatively linked to"), a DNA coding for CSF or a CSF fusion protein.

The invention additionally relates to biologically active derivatives of CSF which can be obtained by modifications, which are known per se, of the DNA sequences. Thus, for example, it is possible to incorporate cleavage sites in the construction of vectors for fusion proteins which, after elimination of the CSF protein, have C-terminal and N-terminal modifications in the amino acid sequence. Furthermore, the invention relates to the use of proteins of this type in medical treatment and to their use of the preparation of medicaments, and to medicaments which contain CSF protein and its biologically active derivatives, in particular medicaments for the stimulation of proliferation of hemopoietic cells and for promotion of the formation of granulocytes and macrophages.

Further aspects of the invention and its preferred embodiments are illustrated in detail below and are defined in the patent claims.

BRIEF DESCRIPTION OF THE DRAWINGS

The invention is furthermore illustrated by FIGS. 1 to 15, each of which explains, mostly in the form of a flow diagram, the processes of the examples of the same numbers. These figures are not to scale, in particular the scale has been "expanded" in the region of the polylinkers.

Thus, FIG. 1 and its continuations 1a and 1b show the preparation of the vector pW 225 which is used for the direct expression of (Met-)CSF. The figures which follow relate to vectors which result in the expression of fusion proteins in which a "ballast" protein, which is derived from a part-sequence of human interleukin-2, hereinafter "IL-2" or "ΔIL-2", is located at the N-terminal end in front of the CSF amino acid sequence:

FIG. 3 shows the synthesis of the vector pW 240 which codes for a fusion protein which results, after acid cleavage, in a CSF derivative which has proline in place of the first amino acid (alanine).

FIG. 4 relates to the preparation of the vector pW 241 which codes for a fusion protein which results, after acid cleavage, in a CSF derivative in which the first amino acid (alanine) is missing.

FIG. 5 demonstrates the preparation of the vector pW 242 which codes for a fusion protein which results, after acid cleavage, in a CSF derivative in which the first five amino acids have been eliminated.

FIG. 6 relates to the preparation of the vector pW 243 which codes for a fusion protein which results, after acid cleavage, in a CSF derivative in which the first seven amino acids are missing.

FIG. 7 shows the synthesis of the vector pW 244 which codes for a fusion protein with which is obtained, after acid cleavage, a CSF derivative in which the first 11 amino acids have been eliminated.

FIG. 10 and its continuation FIG. 10a show the preparation of the hybrid plasmids pS 200 to 204 which contain synthetic CSF DNA part-sequences, the plasmid pS 200 containing "synthesis block I", shown in Appendix I, plasmid pS 201 containing "synthesis block II" shown in Appendix II, plasmid pS 202 containing "synthesis block III" shown in Appendix III, plasmid pS 203 containing the entire synthetic gene, and pS 204 representing an expression plasmid which likewise contains the entire synthetic CSF DNA sequence. Expression and acid cleavage result in the same CSF derivative as described in FIG. 2 being obtained.

FIG. 13 and its continuation 13a show the synthesis of the expression plasmid pS 210 which codes for a fusion protein which provides, after cleavage with cyanogen bromide, a CSF derivative in which all methionine residues have been replaced by neutral amino acids, namely by Ile in position 36 and by Leu in positions 46, 79 and 80.

Finally.

DETAILED DESCRIPTION OF THE PREFERRED EMBODIMENTS

Figure 1:
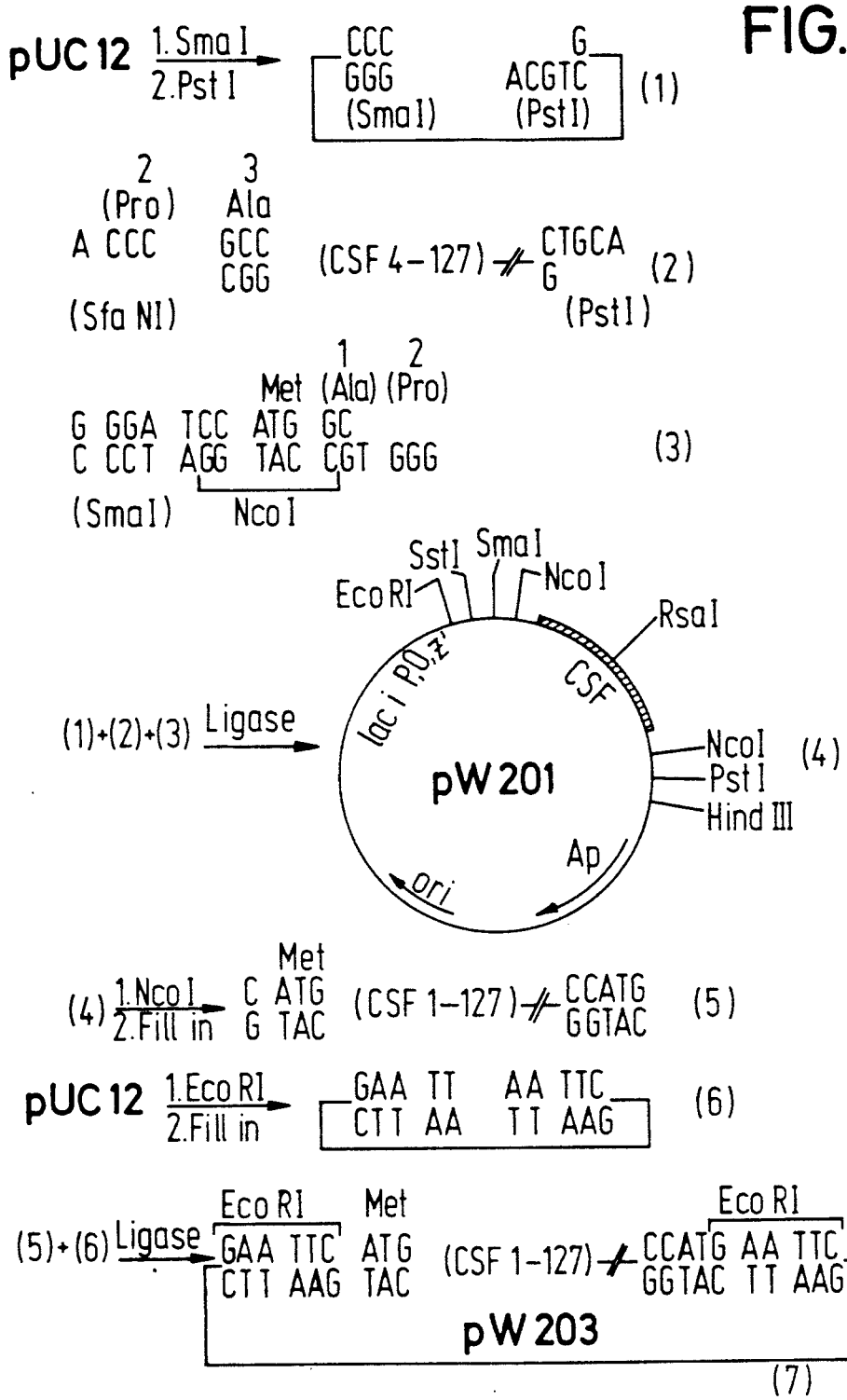
Figure 1B:
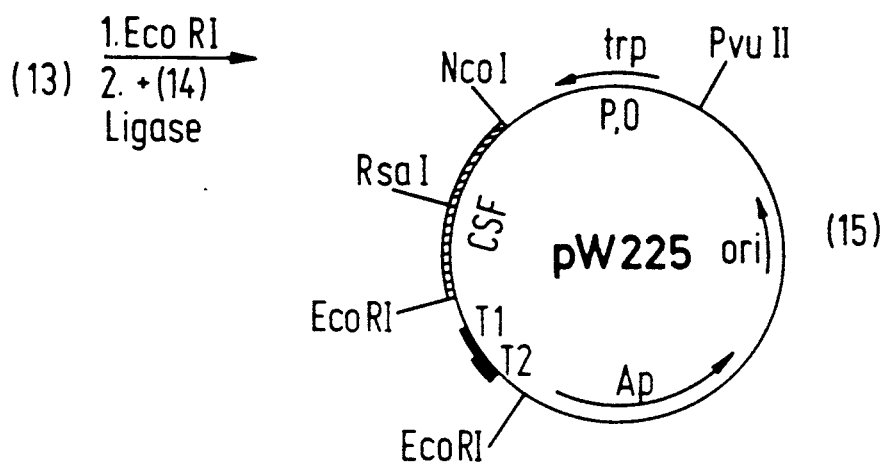

The possible variations explained in these figures and examples are, of course, merely examples of the large numbers of modifications which are possible according to the invention. Thus, it is also possible in a manner known per se to use other protein sequences, especially bacterial, as the "ballast" portion of the fusion proteins, and it is possible to use all customary methods for the linkage and cleavage of the fusion proteins, it being possible for other CSF derivatives with a modified amino acid sequence in the molecule or at both ends of the molecule to result. The choice of the IL-2 sequence and the synthetic DNA sequences and the cleavage of the fusion proteins should thus be viewed merely as preferred embodiments of the invention which can be varied in a manner known per se.

It has emerged that the "open reading frame" comprising a DNA which codes for interleukin-2 is particularly advantageous of an expression aid for the expression of peptides and proteins, and that an N-terminal portion of IL-2 which essentially corresponds to the first 100 amino acids is particularly well suited for the preparation of fusion proteins. The primary product obtained in this way is a fusion protein which is composed entirely or very predominantly of eukaryotic protein sequences. Surprisingly, this protein is apparently not recognized as being a foreign protein by the proteases which are intrinsic to the host, nor is it immediately degraded again. Another advantage is that the fusion proteins according to the invention are sparingly soluble or insoluble and thus can easily be removed, appropriately by centrifugation, from the soluble proteins.

Since, according to the invention, the functioning of the "ballast portion" of the fusion protein does not depend on the IL-2 portion being a biologically active molecule, it likewise does not depend on the exact structure of the IL-2 portion. It suffices for this purpose that essentially the first 100 N-terminal amino acids are present. Thus, it is possible, for example, to carry out at the N-terminal end modifications which permit cleavage of the fusion protein in the case where the desired protein is located N-terminal thereto. Conversely, modifications at the C-terminal end can be carried out in order to permit of facilitate the elimination of the desired protein.

The natural DNA sequence coding for human IL-2 is disclosed in the European Patent Application with the publication number 0,091,539 ("EP-A"). The literature quoted there also relates to mouse and rat IL-2. These mammalian DNAs can be used for the synthesis of the proteins according to the invention. However, it is more appropriate to start from a synthetic DNA, particularly advantageously from the DNA for human IL-2 which has been described in German Offenlegungsschrift 3,419,995 and in the EP-A 0,163,249. This synthetic DNA not only has the advantage that in its choice of codons it is suited to the circumstances in the host which is used most frequently, E. coli, but is also contains a number of cleavage sites for restriction endonucleases at the start and in the region of the 100th triplet, it being possible to make use of these according to the invention. However, this does not rule out modifications to the DNA being carried out in the region lying between them, it being possible to make use of the other cleavage sites.

If use is made of the nucleases Ban II, Sac I or Sst I, then the IL-2 part-sequence which is obtained codes for about 95 amino acids. This length is, in general, sufficient to obtain an insoluble fusion protein. If the lack of solubility is still inadequate, for example in the case of a desired hydrophilic CSF derivative, but it is not wanted to make use of cleavage sites located nearer to the C-terminal end—in order to produce as little "ballast" as possible—then the DNA sequence can be extended at the N-terminal and/or C-terminal end by appropriate adapters or linkers and thus the "ballast" portion can be "tailored" to requirements. Of course, it is also possible to use the DNA sequence—more or less—up to the end and thus generate biologically active IL-2—modified where appropriate—as "by-product".

Thus the invention relates to fusion proteins of the general formula

Met—X—Y—Z    (Ia)

or

Met—Z—Y—X    (Ib)

in which X essentially denotes the amino acid sequence of approximately the first 100 amino acids of, preferably, human IL-2, Y denotes a direct bond in the case where the amino acid or amino acid sequence adjacent to the desired protein allows splitting off of the desired protein, or else denotes a bridge member which is composed of one or more genetically codable amino acids and allows the splitting, and Z is a sequence of genetically codable amino acids representing the desired CSF protein.

As is evident from formulae Ia and Ib—and as already mentioned above too—it is possible to effect expression of the desired protein in front of or behind the IL-2 portion. In order to simplify, hereinafter essentially the second option, which corresponds to the conventional method for the preparation of fusion proteins, will be explained. Thus, although this "classic" variant is described heretofore and hereinafter, this is not intended to rule out the other alternative.

The cleavage of the fusion protein an be carried out chemically or enzymatically in a manner known per se. The choice of the suitable method depends, in particular, on the amino acid sequence of the desired protein. If there is tryptophan or methionine at the carboxyl terminal end of the bridge member Y, or if Y represents Trp or Met, then chemical cleavage with N-bromosuccinimide or cyanogen halide can be carried out in the cases where the particular CSF derivatives which are synthesized do not contain these amino acids.

CSF and those of its derivatives which contain in their amino acid sequence

Asp—Pro and are sufficiently stable to acid can, as already shown above, be cleaved proteolytically in a manner known per se. This results in proteins which contain proline at the N-terminal end or aspartic acid at the C-terminal end being obtained. Thus, it is possible in this way also to synthesize modified proteins.

The Asp-Pro bond can be made even more liable to acid if this bridge member is $(Asp)_n$-Pro or Glu-$(Asp)_n$-Pro, n denoting 1 to 3.

Examples for enzymatic cleavages are likewise known, it also being possible to use modified enzymes having improved specificity (cf. C. S. Craik et al., Science 228 (1985) 291–297).

The fusion protein is obtained by expression in a bacterial expression system in a manner known per se. Suitable for this purpose are all known host-vector systems, such as bacteria of the varieties *Streptomyces, B, B. subtilis, Salmonelia typhimurium* or *Serratia marcescens*, in particular *E. coli*.

The DNA sequence which codes for the desired protein is incorporated in a known manner in a vector which ensures good expression in the selected expression system.

It is appropriate for this to select the promoter and operator from the group comprising trp, lac, tac, $P_L$ or $P_R$ of phage λ, hsp, omp or a synthetic promoter as proposed in, for example, German Offenlegungsschrift 3,430,683 or EP-A 0,173,149. The tac promoter-operator sequence is advantageous, and this is now commercially available (for example expression vector pKK223-3, Pharmacia, "Molecular Biologicals, Chemicals and Equipment for Molecular Biology", 1984, page 63).

It may prove to be appropriate in the expression of the fusion protein according to the invention to modify individual triplets for the first few amino acids after the ATG start codon in order to prevent any base-pairing at the level of the mRNA. Modifications of this type, such as deletions or additions of individual amino acids, are familiar to the expert, and the invention likewise relates to them.

Particularly advantageous CSF derivatives are those containing N-terminal proline, since proteins of this type are more stable to attack by proteases. The CSF derivative which has the entire CSF amino acid sequence following the proline added to the N-terminal end is particularly preferred. However, it has emerged, surprisingly, that the variants of the CSF molecule obtained by elimination of the first 11 amino acids also have biological activity.

Variants of the invention which are also advantageous are those which initially result in fusion proteins which contain the CSF sequence more than once, advantageously twice or three times. By their nature, the ballast portion in these fusion proteins is reduced, and thus the yield of the desired protein is increased.

The plasmid pHG 23 which was obtained by incorporation of the CSF cDNA sequence into the Pst I cleavage site of pBR 322 has been deposited, in *E. coli*, at the American Type Culture Collection under number ATCC 39900. The DNA sequence of this corresponds to the variant described in FIG. 3(B) of Wong et al. The incorporation mode use of the Pst I cleavage site near the 5' end, on the one hand, and of a Pst I site introduced at the 3' end by GC tailing (EP-A 0,183,350).

EXAMPLE 1

Direct Expression of CSF

The commercially available vector pUC 12 is opened with the restriction enzymes Sma I and Pst I, and the large fragment (1) is isolated.

By cutting the cDNA sequence for CSF with the enzymes Sfa NI and Pst I is obtained the fragment (2) which is ligated with the synthetic linker (3) and then with the pUC 12 fragment (1). The hybrid plasmid pW 201 (4) which is thus obtained contains the CSF DNA sequence following the start codon ATG.

The hybrid plasmid (4) is opened with Nco I, and the protruding ends are filled in to give the blunt-ended fragment (5). The vector pUC 12 is opened with the enzyme Eco RI, whereupon the protruding ends are filled in. This is followed by treatment with bovine alkaline phosphatase, the pUC 12 derivative (6) being obtained.

Ligation of the fragments (5) and (6) results in vectors which contain the CSF DNA sequence in both orientations being obtained. They are called pW 203 (7).

Using Eco RI and Rsa I on the vector (7) results in isolation of the fragment (8) which contains the codons for amino acids 63 to 127 of CSF. On the other hand, cutting the vector (4) with Nco I and Rsa I results in isolation of the fragment (9) which contains the codons for amino acids 1 to 61 of CSF.

The plasmid pH 131/5 (German Offenlegungsschrift 3,514,113 or EP-A 0,198,415, Example 1, FIG. 1) (10) is cut with Pvu II, the small fragment is removed, and the larger one is ligated to give the plasmid pPH 160 (11) which is present in *E. coli* cells in a higher copy number than pH 131/5. The plasmid (11) is opened with Nco I and Eco RI, and the large fragment (12) is isolated.

The fragments (8), (9) and (12) are now ligated to give the hybrid plasmid pW 206 (13). This restores the codon for amino acid 62.

The commercially available plasmid pKK 65-10 (PL Biochemical Inc.) is cleaved with Eco RI, and the fragment (14) which contains the two terminators T1 and T2 is isolated. This fragment (14) is inserted into the plasmid (13) which has been opened with Eco RI, the plasmid pW 225 (15) being obtained.

*E. coli* 24 bacteria which contain the plasmid (15) are cultured in LB medium (J. H. Miller, Experiments in Molecular Genetics, Cold Spring Harbor Laboratory, 1972) containing 30 to 50 µg/ml ampicillin at 37° C. overnight. The culture is diluted in the ratio 1:100 with M9 medium (J. M. Miller, op. cit.) which contains 200 µg/l casamino acids and 1 µg/l thiamine, and the mixture is incubated at 37° C. with continuous agitation. At an $OD_{600}=0.5$ or 1 indolyl-3-acrylic acid is added to a final concentration of 15 µg/l, and the mixture is incubated for 2 to 3 hours or 16 hours respectively. The bacteria are then removed by centrifugation. The bacteria are boiled for five minutes in a buffer mixture (7M urea, 0.1% SDS, 0.1M sodium phosphate, pH 7.0), and samples are applied to an SDS gel electrophoresis plate. It emerges that the protein pattern of cells whose trp operon has been induced contains a new protein, in the range of about 14,000–18,000 dalton, which is not found with non-induced cells.

The induction conditions which have been indicated apply to shake cultures; for larger fermentations appropriately modified OD values and, where appropriate, slight variations in the inducer concentrations are advantageous.

EXAMPLE 2

Pro$^O$-CSF

The vector pUC 12 is opened with Eco RI and Pst I, and the large fragment (16) is isolated. This fragment (16) is ligated with the synthetic DNA fragment (17) and the fragment (2) (Example 1; FIG. 1). Competent cells of *E. coli* JM 103 are transformed with the ligation mixture, and the desired clones which contain the plasmid pW 212 (18) are selected.

The fragment (19) which contains the CSF sequence is cut out of the plasmid DNA using Pvu I and Pst I.

Figure 2:
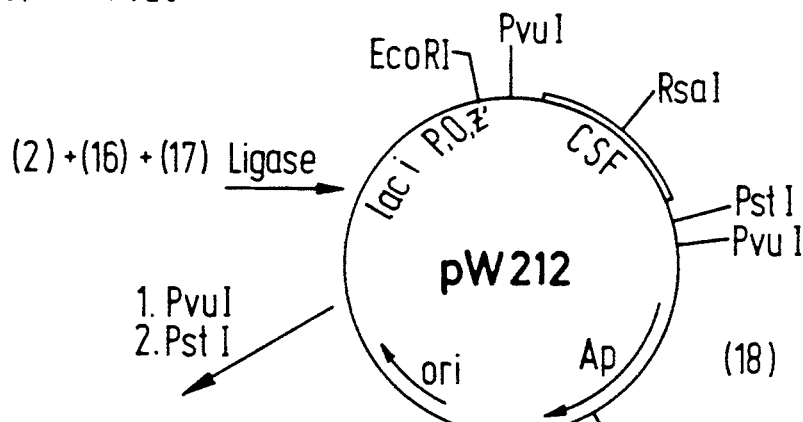
FIG. 2 and its continuations 2a and 2b show the preparation of the vector pW 216 which codes for a fusion protein from which is obtained, by acid cleavage, a CSF derivative which is extended at the N-terminal end by the amino acid proline.

Insertion of the lac repressor (P. J. Farabaugh, Nature 274 (1978) 765–769) into the plasmid pKK 177-3 contain the pUC 8 polylinker (Amann et al., Gene 25 (1983) 167; EP-A 0,133,282) results in the plasmid pJF 118 (20) being obtained (FIG. 2a; cf. German Patent Application P 35 26 995.2, Example 6, FIG. 6). The latter is opened at the unique restriction site for Ava I, and is reduced in size by about 1,000 bp by exonuclease treatment in a manner known per se. Ligation results in the plasmid pEW 1000 (21) being obtained, in which the lac repressor gene is completely retaining but which, because of the reduction in size, is present in a markedly higher copy number than the initial plasmid.

In place of the plasmid pKK 177-3, it is also possible to start from the above-mentioned commercially available plasmid pKK 223-3, to incorporate the lac repressor, and to shorten the resulting product analogously.

The plasmid pEW 1000 (21) is opened with the restriction enzymes Eco RI and Sal I, and the fragment (22) is isolated.

The plasmid p159/6 (23), prepared as described in German Offenlegungsschrift 3,419,995 (EP-A 0,163,249), Example 4 (FIG. 5), is opened with the restriction enzymes Eco RI and Sal I, and the small fragment (24), which contains the IL-2 sequence, is isolated.

The hybrid plasmid pEW 1001 (25) is obtained by ligation of the fragments (22) and (24).

On the one hand, the plasmid (25) is opened with Eco RI and Pvu I, the fragment (26) which contains the largest part of the IL-2 sequence being obtained. This part-sequence is denoted "ΔIL2" in the figures.

On the other hand, the plasmid (25) is opened with Eco RI and Pst I, and the large fragment (27) is isolated.

Ligation of the fragments (19), (26) and (27), transformation of competent *E. coli* 294 cells, and selection results in clones which contain the plasmid pW 216 (28) being obtained. The plasmid DNA is characterized by restriction analysis and DNA sequence analysis.

An overnight culture of *E. coli* cells which contain the plasmid (28) is diluted with LB medium (J. M. Miller, op. cit.), which contains 50 μg/ml ampicillin, in the ratio of about 1:100, and the growth is followed via measurement of the OD. At OD=0.5, the culture is adjusted to 1 mM in isopropyl β-galactopyranoside (IPTG) and, after 150 to 180 minutes, the bacteria are removed by centrifugation. The bacteria are boiled for five minutes in a buffer mixture (7M urea, 0.1% SDS, 0.1M sodium phosphate, pH 7.0), and samples are applied to an SDS gel electrophoresis plate. Following electrophoresis, a protein band which corresponds to the size of the expected fusion protein is obtained from bacteria which contain the plasmid (28). After disruption of the bacteria (French press, ®Dyno mill) and centrifugation, the fusion protein is located in the sediment so that it is possible already to remove considerable amounts of the other proteins with the supernatant. Isolation of the fusion protein is followed by acid cleavage to liberate the expected CSF derivative which contains an additional N-terminal proline. This shows activity in the biological test.

The induction conditions which have been indicated apply to shake cultures; for larger fermentations appropriately modified OD values and, where appropriate, slight variations in the IPTG concentrations are advantageous.

EXAMPLE 3

Pro$^1$-CSF(2-127)

Ligation of the fragments (2) (FIG. 1) and (10) (FIG. 2) with the synthetic DNA sequence (29) results in the hybrid plasmid (30) which corresponds to the plasmid (18) apart from the synthetic DNA sequence.

Pvu I and Pst I are used to cut out of the plasmid (30) the fragment (31) which contains the CSF DNA sequence in which, however, the codon for the first amino acid has been replaced by a codon for proline. Ligation of the fragment (31) with the fragments (26) and (27) results in the hybrid plasmid pW 240 (32) being obtained. Expression in *E. coli*, which is carried out as in Example 2, provides a CSF derivative in which the first amino acid has been replaced by proline. This derivative also shows biological activity.

EXAMPLE 4

CSF(2-127)

A plasmid which contains the CSF DNA sequence with a Pst I restriction site at its 3' end, for example the plasmid pHG 23 (ATGG 39900), is cleaved with Sfa NI, and the linearized plasmid (34) is partially filled in using Klenow polymerase and GTP. The protruding nucleotide A is eliminated using S1 nuclease, and then the fragment (35) is cut out with Pst I.

Ligation of the fragment (35) with the synthetic DNA sequence (36) and the fragment (16) (FIG. 2) results in the plasmid (37), which is analogous to plasmid (18), being obtained.

Pvu I and Pst I are used to cut the fragment (38) out of the plasmid (37). This fragment is ligated with the fragments (26) and (27), by which means the plasmid pW 241 (39) is obtained.

Expression as in Example 2 results in a fusion protein which, after acid cleavage, provides a CSF derivative missing the first amino acid. This derivative is biologically active.

EXAMPLE 5

CSF(6-127)

The plasmid (33) (or a corresponding plasmid which contains the CSF DNA sequence) is first totally cleaved with Pst I and then partially cleaved with Bst NI, and the fragment (40) is isolated.

The synthetic DNA sequences (41) and (36) (FIG. 4) are first ligated to give the sequence (42), and the latter is then ligated with the fragment (40) and the fragment (16) (FIG. 2), the plasmid pW 212 (43) being obtained.

Pvu I and Pst I are used to isolate from the plasmid (43) the fragment (44) which contains the DNA sequence for the CSF derivative. This fragment (44) is ligated with the fragments (26) and (27), which results in the hybrid plasmid pW 242 (45).

Expression as in Examples 2 results in a fusion protein from which is obtained, after acid cleavage, a CSF derivative missing the first five amino acids. This product is also biologically active.

EXAMPLE 6

CSF(8-127)

When first the synthetic DNA sequence (36) (FIG. 4) is ligated with the synthetic DNA sequence (46), and thereafter the resulting DNA fragment (47) is ligated with the fragments (40) and (16), then the hybrid plasmid (48) is obtained. Pvu I and Pst I are used to cut out of the latter the fragment (49) which contains the DNA sequence for the CSF derivative. Ligation of the fragments (49), (26) and (27) provides the hybrid plasmid pW 243 (90) which corresponds to the plasmid (45) apart from the shortened DNA sequence for the CSF derivative.

Expression as in Example 2 results in a fusion protein which, after acid cleavage, provides a CSF derivative missing the first seven amino acids. This derivative is also biologically active.

EXAMPLE 7

CSF(12-127)

When the synthetic DNA sequence (51) is ligated with the fragments (33) and (16) then the hybrid plasmid (52) is obtained. When Pvu I and Pst I are used to cut out of the latter the sequence (53), which contains the DNA sequence for the CSF derivative, and this fragment (53) is ligated with the fragments (26) and (27) then the hybrid plasmid pW 244 (54) which corresponds to the plasmid (45) apart from the shortened CSF sequence is obtained.

Expression as in Example 2 results in a fusion protein which, after acid cleavage, provides a CSF derivative from which amino acids 1 to 11 have been eliminated. This shortened molecule is also biologically active.

EXAMPLE 8

Pro$^O$-CSF(1-126)-Asp

The DNA sequence (19) (FIG. 2) is partially cleaved with Bst NI, and the fragment (55), which contains the largest part of the CSF sequence, is isolated.

Cleavage of the plasmid (33) (FIG. 4) (or of a corresponding plasmid which contains the CSF DNA sequence) first with Pst I and then partially with Bst NI results in the DNA sequence (56) which comprises the largest part of the CSF sequence being obtained.

The DNA sequence (57) is synthesized which together with the sequence (56) provides a DNA sequence which codes for a CSF derivative in which the C-terminal glutamic acid has been replaced by aspartic acid.

The vector pUC 13 is opened with Pst I and Sma I, and the large fragment (58) is isolated. When this linearized plasmid (58) is ligated with the fragments (56) and (57), then the hybrid plasmid pW 245 (59) with the modification of the C-terminal sequence is obtained.

Figure 8A:
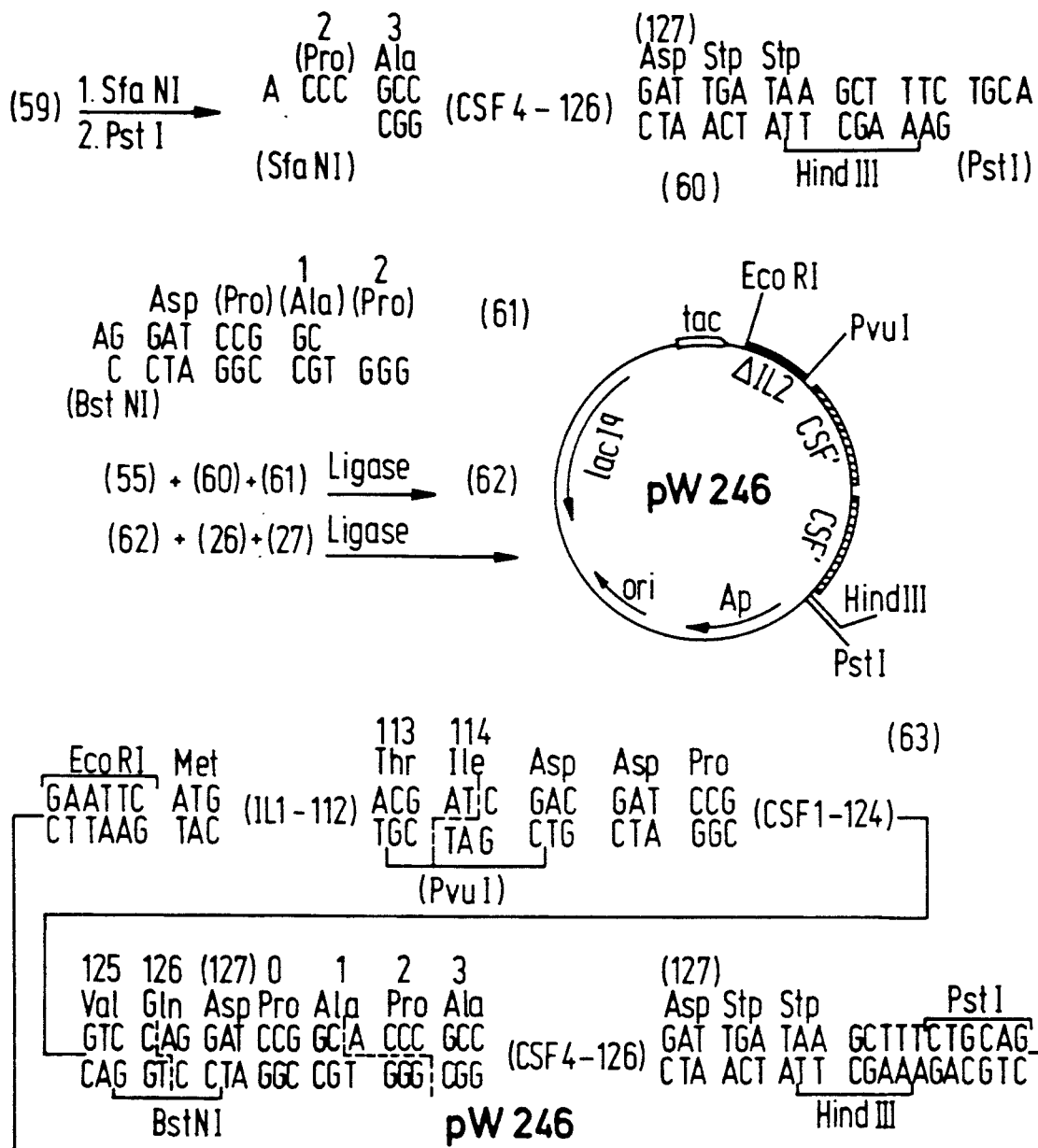
FIG. 8 and its continuation 8a show the synthesis of the vector pW 246. This codes for a fusion protein in which two modified sequences, denoted "CSF", follow the IL-2 part-sequence. Acid cleavage results in a CSF derivative in which proline is located at the N-terminal end in front of the first amino acid proline and in which the last amino acid has been replaced by aspartic acid.
Figure 9:
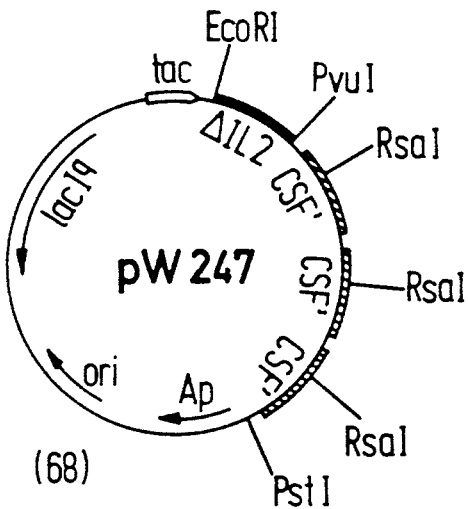
FIG. 9 shows the synthesis of the vector pW 247 which codes for a fusion protein in which three CSF' sequences follow the IL-2 part-sequence. Acid cleavage results in the CSF derivative characterized in FIG. 8 being obtained.

Sfa NI and Pst I are used to cut out of the plasmid (59) the fragment (60) which contains the modified CSF DNA sequence. This fragment (60) is ligated with the synthetic DNA sequence (61) and the fragment (55), the DNA sequence (62) being obtained. The latter is ligated with the DNA fragments (26) and (27) (FIG. 2), the hybrid plasmid pW 246 (63) being obtained. This plasmid is shown twice in FIG. 8a, the lower representation indicating the amino acid sequence of the coded fusion protein.

Expression as in Example 2 results in a fusion protein from which, after acid cleavage, is derived a CSF derivative which is extended by an N-terminal proline and in which, additionally, the final amino acid has been replaced by aspartic acid. This derivative is biologically active.

EXAMPLE 9

Pro$^O$-CSF(1-126)-Asp

The hybrid plasmid (63) (FIG. 8) is cleaved with Eco RI and Pst I, and the fragment which contains the two modified CSF sequences following the IL-2 part-sequence is isolated. This sequence (64) is partially cleaved with Rsa I, and the two fragments (65) and (66) are isolated. The fragment (66) is cleared with Bst NI, and the fragment (67) is isolated. Ligation of the DNA sequences (27), (65), (67), (61) and (60) results in the hybrid plasmid pW 247 (68) in which the ligated sequences are arranged in the specified sequence.

Expression as in Example 2 provides a fusion protein from which results, after acid cleavage, the same CSF derivative as in Example 8.

EXAMPLE 10

Synthetic Gene (for Pro$^O$-CSF)

Processes known per se, for example the phosphite method (German Offenlegungsschriften 3,327,007, 3,328,793, 3,409,966, 3,414,831 and 3,419,995) are used to synthesize the three "synthesis blocks" I (CSF-I), designated (69) in the figures, II (CSF-II), (70) in the figures, and III (CSF-III), (71) in the figures. The synthesized oligonucleotides Ia to Im, IIa to IIf and IIa to IIl1 are indicated in the nucleotide sequence of these synthesis blocks (Appendix).

The choice of the nucleotides for the synthetic gene entailed provision not only of unique cleavage sites at the points of union of the three synthesis blocks but also of a number of unique restriction sites inside the gene fragments. These are listed in the tables below. These unique restriction sites can be used, in a manner known per se, to exchange, add, or delete codons for amino acids.

| Enzyme | Recognition sequence | Cut after nucleotide no. (coding strand) |
|---|---|---|
| | Synthesis Block I (CSF I) | |
| Nar I | GG ↓ CGCC | 1 |
| Hpa II | C ↓ CGG | 4 |
| Hae II | GGCGC ↓ C | 4 |
| Nae I | GCC ↓ GGC | 5 |
| Pvu I | CGAT ↓ CG | 13 |
| Sal I | G ↓ TCGAC | 24 |
| Acc I | GT ↓ CGAC | 25 |
| Hinc II | GTC ↓ GAC | 26 |
| Hpa I/ Hinc II | GTT ↓ AAC | 48 |
| Hha I | GCG ↓ C | 66 |
| Hinf I | G ↓ AGTC | 88 |
| Nru I | TCG ↓ CGA | 89 |
| Xma III | C ↓ GGCCG | 95 |
| Sac II | CCGC ↓ CG | 101 |
| Eco RV | GAT ↓ ATC | 128 |
| | Synthesis Block II (CSF-II) | |
| Afl III | A ↓ CATGT | 147 |

-continued

| Enzyme | Recognition sequence | Cut after nucleotide no. (coding strand) |
|---|---|---|
| Mlu I | A ↓ CGCGT | 169 |
| Xho I | C ↓ TCGAC | 175 |
| Taq I | T ↓ CGA | 176 |
| Hga I | GACGC (5/10) | 177 |
| Ava I | C ↓ TCGAG | 177 |
| Alu I | AG ↓ CT | 180 |
| Sac I/ Hgi AI | GAGCT ↓ C | 182 |
| Stu I/ Hae I | AGG ↓ CCT | 194 |
| Synthesis Block III (CSF-III) | | |
| Afl II | C ↓ TTAAG | 217 |
| Hae III | GG ↓ CC | 224 |
| Apa I | GGGCC ↓ C | 227 |
| Mnl I | CCTC (7/7) | 238 |
| Nhe I | G ↓ CTAGC | 241 |
| Mae I | C ↓ TAG | 242 |
| Aha II | GA ↓ CGTC | 280 |
| Aat II | GACGT ↓ C | 283 |
| Sci NI | G ↓ CGC | 287 |
| Mst I | TCG ↓ GCA | 288 |
| Sau 3AI/ Mbo I | ↓ GATC | 296 |
| Dpn I | GA ↓ TC | 298 |
| Asu II | TT ↓ CGAA | 308 |
| Aha III | TTT ↓ AAA | 318 |
| Ava II | G ↓ GTCC | 382 |
| Eco RII | ↓ CCAGG | 384 |
| Bst NI/ Scr FI | CC ↓ AGG | 380 |

The three synthesis blocks were first individually cloned, amplified in *E. coli* and re-isolated:

Synthesis block CSF-I (69) is incorporated in the pUC 12 derivative (16), the plasmid pS 200 (72) being obtained.

pUC 12 is opened with the restriction enzymes Pst I and Hind III and the linearized plasmid (73) is ligated with synthesis block CSF-II (70), the plasmid pS 201 (74) being obtained.

pUC 13 is opened with Hind III and Sma I, and the linearized plasmid (75) is ligated with CSF-III (71), the plasmid pS 202 (76) being obtained.

The re-isolated synthesis blocks (69), (70) and (71) are now ligated in the vector pUC 12 (77) which has been linearized with Eco RI and Sma I, the result being the plasmid pS 203 (78). This hybrid plasmid is—as the plasmids with the individual synthesis blocks—amplified in *E. coli* 79/102, and the synthetic gene is characterized by restriction analysis and sequence analysis.

The plasmid (78) is cleaved with Pvu I partially and with Bam HI, and the small fragment (79) with the complete CSF sequence is isolated.

The expression plasmid (21) is opened with Eco RI and Bam HI, and the large fragment (80) is isolated. This fragment (80) is now ligated with the fragment (26) which contains the IL-2 part-sequence and the synthetic gene (79). This results in the plasmid pS 204 (81) which codes for a fusion protein in which the IL-2 part-sequence is followed first by the bridge member which permits acid cleavage and then by the amino acid sequence of CSF. Thus, acid cleavage results in a CSF derivative which is extended by proline at the N-terminal end.

EXAMPLE 11

CSF(1-12)His(14-121)His(123-127)

When the nucleotides in synthesis block I up to No. 48 (cleavage site for Hpa I) are replaced by the synthetic sequences (82) and (83), then the result is a modified synthesis block I which codes for a CSF I analog in which there is Trp in front of the first amino acid (Ala), and Trp in position 13 has been replaced by His.

The plasmid (72) (FIG. 10) is opened with Eco RI and Hpa I, and the large fragment (84) is isolated. The latter is now ligated with the synthetic fragments (82) and (83), the plasmid pS 205 (85) which codes for this modified CSF I (CSF I') being obtained.

The plasmid (76) (FIG. 10) is opened with Hind III and Sal I, and the small (86) and large (87) fragments are isolated. The small fragment (86) is then cut with Taq I, and the fragment (88) is isolated.

The large fragment (87) is now ligated with (88) and with the synthetic fragment (89) in which the codon for Trp in position 122 has been replaced by His, the plasmid pS 206 (90) which codes for the modified CSF III (CSF III') being obtained. This plasmid is transformed into *E. coli*, amplified, re-isolated, cut with Hind III and Sal I, and the small fragment (91) which codes for CSF III' is isolated.

The plasmid (85) is cut with Pvu I partially and with Pst I, and the small fragment (92) which codes for CSF I' is isolated.

When the fragments (22), (26), (92), (70) and (91) are now ligated then the plasmid pS 207 (93) is obtained. This codes for a fusion protein in which the IL-2 part-sequence is followed by a bridge member which contains Trp immediately in front of the first amino acid of CSF (Ala). Since Trp in positions 13 and 122 of the CSF molecule have been replaced by His, it is now possible to cleave the fusion protein with N-bromosuccinimide. This results in the CSF derivative in which tryptophan in both positions has been replaced by histidine.

EXAMPLE 12

CSF(1-99)Thr(101-127)

When, in the synthesis of the synthesis block III, oligonucleotides IIIe and IIIf are replaced by the synthetic sequence (94) and the process is otherwise carried out as in Example 10, then a CSF derivative in which Ile in position 100 has been replaced by Thr is obtained.

EXAMPLE 13

CSF(1-35)Ile(37-45)Leu(47-78)Leu-Leu(81-127)

First the oligonucleotide (95) which contains in position 36 the codon for Ile in place of Met, and the oligonucleotide (96) in which the codon for Met in position 46 has been replaced by a codon for Leu, are synthesized.

The plasmid (72) (FIG. 10) is then opened with Pvu I and Xma III, and the fragment (97) is isolated.

In addition, the sequence (98) in which the codon for Met is located in front of that for the first amino acid is synthesized.

When the fragments (16), (98), (97), (95) and (96) are now ligated then the plasmid pS 208 (99) is obtained. This corresponds to the plasmid (72) but contains in position 0 of the CSF I sequence the codon for Met, in position 36 a codon for Ile, and in position 46 a Codon for Leu.

In addition, the sequence (100) which in positions 79 and 80 codes for Leu in place of Met is synthesized.

When the plasmid (76) (FIG. 10) is opened with Hind III and Nhe I, and the large fragment (101) is isolated and ligated with the synthetic sequence (100), then the plasmid pS 209 (102) which corresponds to the plasmid

(76) part from replacement of the two codons in positions 79 and 80 in the CSF III sequence is obtained.

Figure 11A:
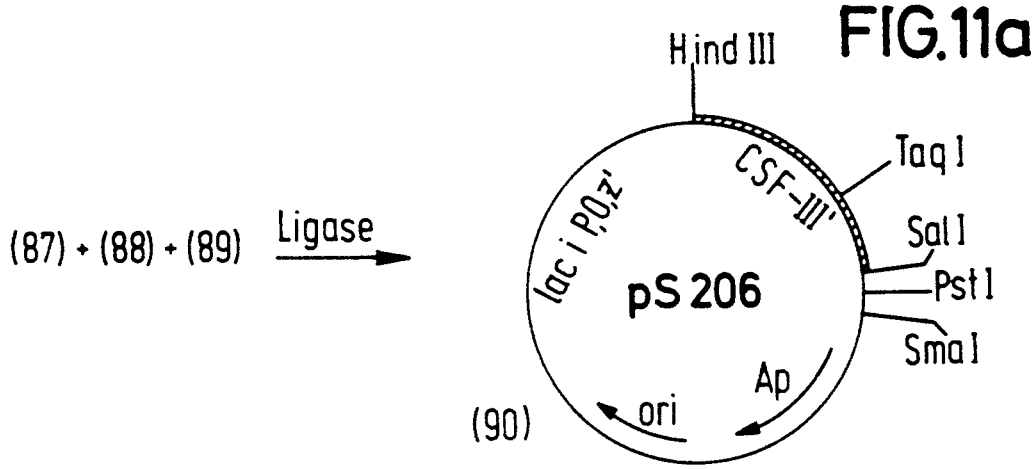
FIG. 11 and its continuation FIG. 11a show the synthesis of the expression plasmid pS 207 which codes for a fusion protein which provides, after cleavage with N-bromosuccinimide, a CSF derivative in which Trp in each of positions 13 and 122 has been replaced by His.
Figure 12:
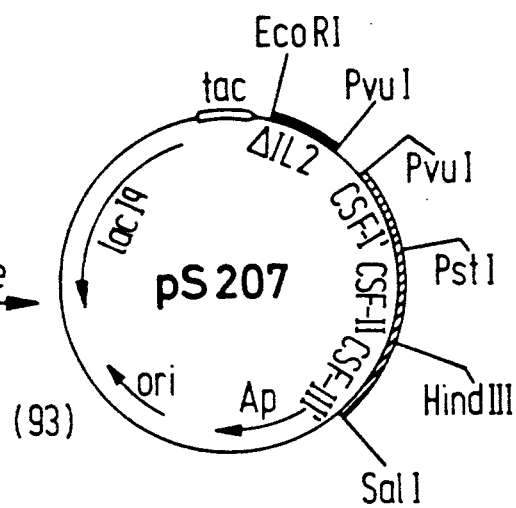
FIG. 12 shows a synthetic DNA part-sequence which permits the preparation of a CSF derivative in which Ile in position 100 has been replaced by Thr.
Figures 13A, 14, 15:
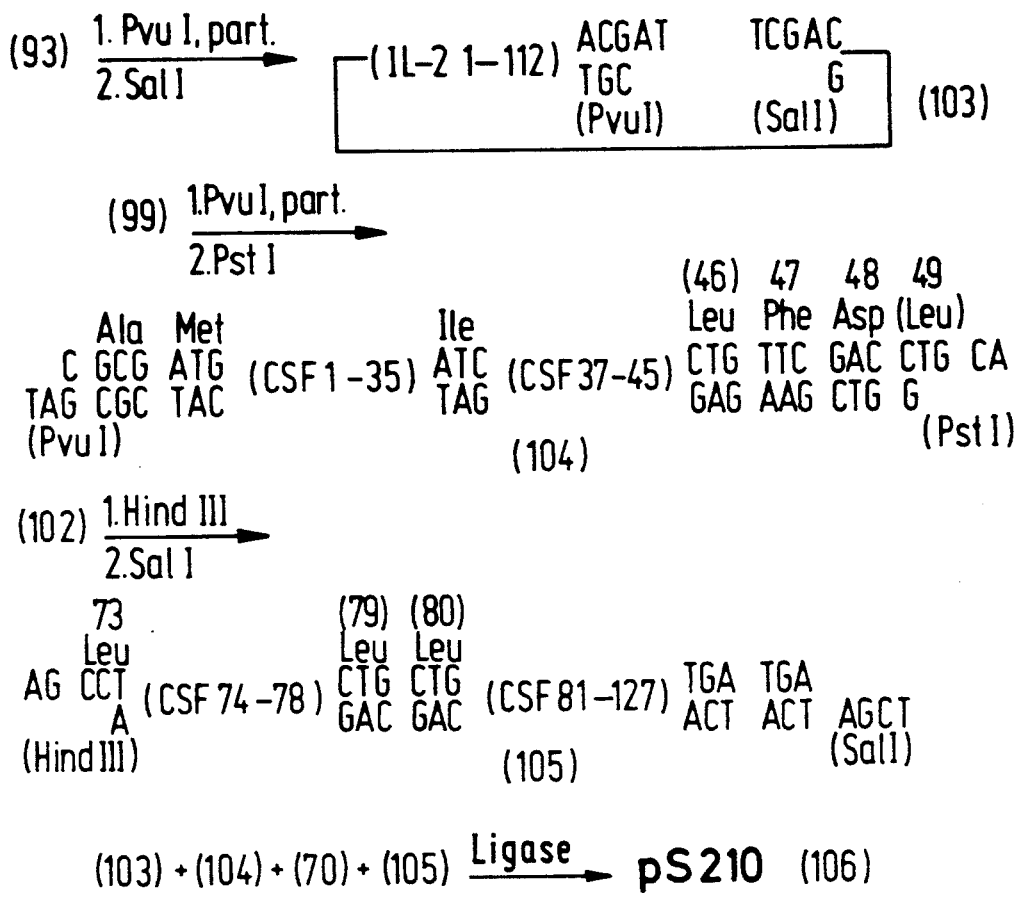
FIG. 14 shows a synthetic DNA sequence which permits, in accordance with the synthesis scheme in FIG. 13, the preparation of a CSF derivative in which Met in position 36 has been replaced by Ile, and Met in position 46 has been replaced by Leu, and a single Leu residue is present in place of amino acids 79 and 80.
FIG. 15 shows a synthetic DNA whose use in the synthesis scheme shown in FIG. 13 permits the preparation of a CSF derivative in which Met in position 36 has been replaced by Ile and in position 46 has been replaced by Leu, and in which the two amino acids in positions 79 and 80 have been deleted.

The plasmid (93) (FIG. 11a) is now partially cut with Pvu I and with Sal I, and the large fragment (103) is isolated. The plasmid (99) is likewise partially opened with Pvu I and with Pst I, and the small fragment (104), which contains the modified CSF I sequence is isolated. In addition, the plasmid (102) is opened with Hind III and Sal I, and the small fragment (105), which comprises the modified CSF III sequence is isolated.

The fragments (103), (104), (70) and (105) are now ligated, there being obtained the plasmid pS 210 (106) which corresponds to the plasmid (93) (FIG. 11a) but codes for a CSF derivative which has Met in position 0 and in which, on the other hand, the four Met residues have been replaced by the other amino acids.

When E. coli is transformed with the plasmid (106) then, after induction, a fusion protein is obtained which can be cleaved with cyanogen halide resulting in a CSF derivative which contains Ile in position 36 and Leu in positions 46, 79 and 80.

EXAMPLE 14

CSF(1-35)Ile(57-45)Leu(47-78)Leu(81-127)

When the process is carried out as in Example 13, but the synthetic sequence (107) is used in place of the synthetic sequence (100), then a deletion product which has Ile in position 36 and Leu in position 46, and in which the amino acid Leu is present in place of amino acids 79 and 80, is obtained.

EXAMPLE 15

CSF(1-35)Ile(37-45)Leu(47-78)-(81-127)

When the process is carried out as in Example 13 but the synthetic sequence (108) is used in place of the synthetic sequence (100), then a deletion product which has Ile in position 36 and Leu in position 46, and in which the amino acids in positions 79 and 80 have been deleted, is obtained.

APPENDIX

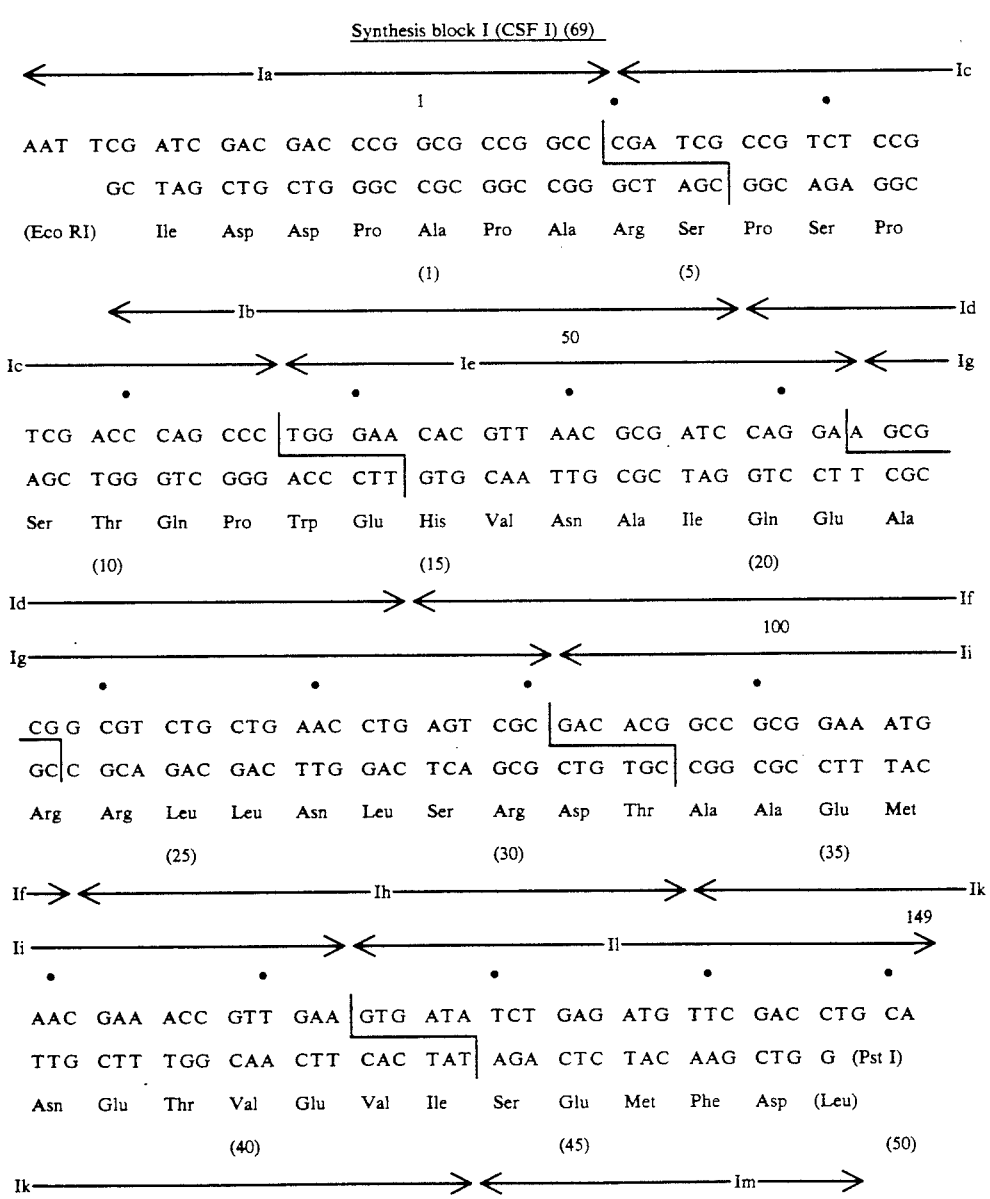

-continued

Synthesis block II (CSF II) (70)

```
          150
         <─────────── IIa ──────────────>  <──────────── IIc
           •              •              •              •
(Pst I) G  GAA  CCG  ACA  TGT  CTC  CAG  ACG │CGT  CTC  GAG  CTC  TAC
     AC    CTT  GGC  TGT  ACA  GAG  GTC  TGA│ GCA  GAG  CTC  GAG  ATG
      (Gln) Glu  Pro  Thr  Cys  Leu  Gln  Thr  Arg  Leu  Glu  Leu  Tyr
            (50)                (55)                (60)

<──────────── IIb ───────────────────>   <────── IId
                      200              214
IIc ────>  <────── IIe ──────>
     •              •              •              •
     AAA  CAA  GGC │CTT  CGT  GGT  TCT  CTG  ACC  A  (Hind III)
     TTT  GTT  CCG  GAA  GCA│ CCA  AGA  GAC  TGG  TTC  GA
     Lys  Gln  Gly  Leu  Arg  Gly  Ser  Leu  Thr  (Lys)
           (65)                (70)

IId ─────────────>  <────── IIf ─────>
```

Synthesis block III (CSF III) (71)

```
          215                                                    250
         <──────────── IIIa ─────────────────>  <──────── IIIc
           •              •              •              •
     AG   CTT  AAG  GGG  CCC  CTC  ACC  ATG  ATG  GCT  AGC  CAC │TAC  AAA
(Hind III) A   TTC  CCC  GGG  GAG  TGG  TAC  TAC  CGA  TCG  GTG  ATG  TTT│
         (Leu) Lys  Gly  Pro  Leu  Thr  Met  Met  Ala  Ser  His  Tyr  Lys
         (72)        (75)                (80)                (85)

<──────────── IIIb ─────────────────>
IIIc ─────────────────────────────>  <──────────────── IIIe
     •              •              •              •
     CAG  CAC  TGC  CCG  CCG  ACT  CCG  GAG  ACG │TCT  TGC  GCA  ACG  CAG
     GTC  GTG  ACG  GGC  GGC  TGA  GGC  CTC  TGC  AGA  ACG│ CGT  TGC  GTC
     Gln  His  Cys  Pro  Pro  Thr  Pro  Glu  Thr  Ser  Cys  Ala  Thr  Gln
                       (90)                (95)

<──────────── IIId ─────────────────>  <──────── IIIf
          300
IIIe ────>  <──────────── IIIg ─────────────────>
     •              •              •              •
     ATC  ATC │ACC  TTC  GAA  TCT  TTT  AAA  GAA  AAC  CTG  AAG  GAC  TTT
     TAG  TAG  TGG  AAG│ CTT  AGA  AAA  TTT  CTT  TTG  GAC  TTC  CTG  AAA
     Ile  Ile  Thr  Phe  Glu  Ser  Phe  Lys  Glu  Asn  Leu  Lys  Asp  Phe
         (100)               (105)               (110)

IIIf ─────────────>  <─────────────────────────────── IIIh
                      350                                        391
         <──────────── IIIi ─────────────────>  <──────── IIIk
           •              •              •              •        ••
     │CTG  CTT  GTT  ATA  CCG  TTC  GAC  TGT  TGG  GAG │CCG  GTC  CAG  GAA
      GAC  GAA│ CAA  TAT  GGC  AAG  CTG  ACA  ACC  CTC  GGC  CAG│ GTC  CTT
      Leu  Leu  Val  Ile  Pro  Phe  Asp  Cys  Trp  Glu  Pro  Val  Gln  Glu
         (115)               (120)               (125)
```

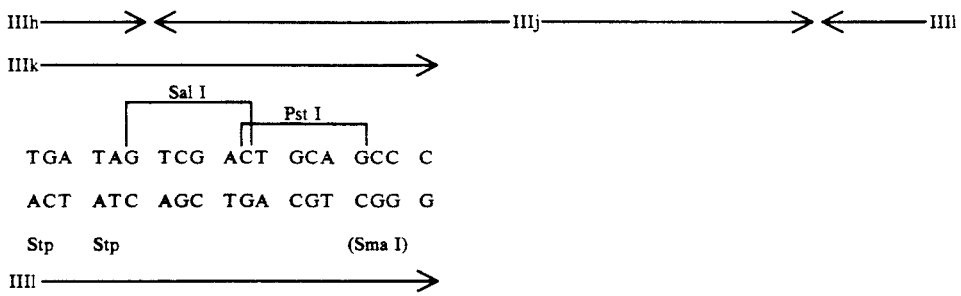
We claim:
1. A human GM-CSF derivative comprising an amino acid sequence of the formula
Pro—(As)$_x$—CSF(12-126)—Z,
wherein (As)$_x$ denotes all or some of the first 11 amino acids of natural human GM-CSF sequence without substitution, CSF(12-126) denotes 12th to 126th amino acids of the natural human GM-CSF sequence, and Z denotes Glu or Amp.
* * * * *

UNITED STATES PATENT AND TRADEMARK OFFICE
CERTIFICATE OF CORRECTION

PATENT NO. : 5,298,603
DATED : March 29, 1994
INVENTOR(S) : Paul Habermann et al.

It is certified that error appears in the above-identified patent and that said Letters Patent is hereby corrected as shown below:

Claim 1, column 18, penultimate line, change "Amp" to --Asp--.

Signed and Sealed this

Sixth Day of December, 1994

Attest:

BRUCE LEHMAN

*Attesting Officer*     *Commissioner of Patents and Trademarks*